(12) United States Patent
Högdahl

(10) Patent No.: US 8,172,797 B2
(45) Date of Patent: May 8, 2012

(54) MEDICAL DELIVERY DEVICE

(75) Inventor: Stefan Högdahl, Stockholm (SE)

(73) Assignee: SHL Group AB, Nacka Strand (SE)

( * ) Notice: Subject to any disclaimer, the term of this patent is extended or adjusted under 35 U.S.C. 154(b) by 0 days.

(21) Appl. No.: 12/681,960

(22) PCT Filed: Oct. 7, 2008

(86) PCT No.: PCT/EP2008/063394
§ 371 (c)(1),
(2), (4) Date: Apr. 16, 2010

(87) PCT Pub. No.: WO2009/047247
PCT Pub. Date: Apr. 16, 2009

(65) Prior Publication Data
US 2010/0222742 A1 Sep. 2, 2010

(30) Foreign Application Priority Data

Oct. 10, 2007 (SE) ..................................... 0702270
Feb. 4, 2008 (SE) ..................................... 0800258

(51) Int. Cl.
*A61M 37/00* (2006.01)
*A61M 5/20* (2006.01)
*A61M 5/315* (2006.01)

(52) U.S. Cl. .................. 604/141; 604/135; 604/218

(58) Field of Classification Search .................. 604/135
See application file for complete search history.

(56) References Cited

U.S. PATENT DOCUMENTS

| 5,599,302 | A | * | 2/1997 | Lilley et al. | 604/68 |
|---|---|---|---|---|---|
| 6,258,068 | B1 | * | 7/2001 | Kirchhofer et al. | 604/208 |
| 6,454,743 | B1 | * | 9/2002 | Weber | 604/131 |
| 7,416,540 | B2 | * | 8/2008 | Edwards et al. | 604/144 |
| 2003/0233070 | A1 | * | 12/2003 | De La Serna et al. | 604/141 |
| 2004/0215151 | A1 | * | 10/2004 | Marshall et al. | 604/198 |
| 2005/0171477 | A1 | * | 8/2005 | Rubin et al. | 604/156 |
| 2007/0100292 | A1 | * | 5/2007 | Kirchhofer et al. | 604/208 |

FOREIGN PATENT DOCUMENTS
WO WO 2006058426 A1 * 6/2006
* cited by examiner

*Primary Examiner* — Nicholas Lucchesi
*Assistant Examiner* — Jenna Zhang
(74) *Attorney, Agent, or Firm* — Potomac Patent Group PLLC

(57) ABSTRACT

The present invention relates to an injection device comprising a housing, a container containing medicament to be injected through a needle (34) attachable to said container, drive means (46) operatively acting on said container for injecting said medicament, the drive means comprising a gas spring (50), locking (57) and activating means (56) arranged to hold said gas spring in a loaded state, and when activated, releases said gas spring to inject said medicament.

5 Claims, 5 Drawing Sheets

MEDICAL DELIVERY DEVICE

This application claims the benefit of the filing date of and priority from International Application No. PCT/EP2008/063394 filed on Oct. 7, 2008, and Swedish Patent Applications No. 0800258-6 and No. 0702270-0 filed on Oct. 10, 2007, and Feb. 4, 2008, respectively.

TECHNICAL AREA

The present invention relates to a medical delivery device and in particular a medicament injection device.

TECHNICAL BACKGROUND

The field of medicament delivery devices is becoming increasingly important, and in particular injection devices for self-administration of medicament is becoming more and more popular.

However, there are a few aspects that affect the possibilities of successfully marketing an injection device, satisfying requirements from both injector manufacturers, drug manufacturers and of course the users of the devices.

Regarding manufacturing and sales of injection devices one requirement is that it must not be too expensive to manufacture, and the cost is very much depending on the complexity of the device regarding functions because added functions mean additional components that have to be designed so that they interact flawlessly in order to ascertain proper function of the device. Regarding the sales and end users, the device should preferably be rather discrete at the same time as it should be easy to use, almost intuitive at the same time as it should be safe enough to avoid unintentional firing of the device.

Another aspect regarding medicament delivery devices is how to expel the medicament. Often the medicament is arranged in a compartment having a movable wall, like a stopper, and an orifice in the opposite end, to which orifice a needle is attached, like a syringe or cartridge.

Often a spring or the like force means is connected to a plunger rod, in turn acting on the stopper for expelling the medicament. The spring is in most applications a helically wound compression spring, which is a well tried and economical drive member for an injection device. However, it has a few drawbacks that can affect the function of the device. One drawback is that the spring force is highest at the beginning of the movement of the plunger rod, and that the spring force decreases linearly with the extension of the spring, until it reaches almost zero force when almost fully extended. If the medicament has a rather high viscosity, it requires rather high forces to push it through the narrow passage of the needle, where the forces have to be available during the whole stroke of the plunger rod. With a compression spring, it has to be "over-dimensioned" in order to handle the whole stroke.

Another drawback with the compression spring can be that the force is highest at the beginning of the stroke, and if a sudden high force is applied to the cartridge or syringe often mad of glass, it may break, causing a serious malfunction of the device.

Attempts have been made to arrange force members providing more constant force during the stroke, for example leaf springs. However, they tend to require more space than spiral springs, thus making the devices larger.

Attempts have also been made to arrange force members providing more constant force during the stroke, for example gas springs as in US2004/0254525, US2002007149 and U.S. Pat. No. 5,919,159. However, these members have been only provided in needle-less delivery devices which require high driving pressure without damping for driving the drug through a nozzle into the outermost layer of the skin. Since the thickness and penetrability of the skin varies from patient to patient, it is complicated to regulate the level of pressure to drive the drug correctly through the outermost layer of the skin and many patients experience said needle less injections as painfully.

BRIEF DESCRIPTION OF THE INVENTION

There is thus a need exists for an improved injection device using a needle wherein the force member provides more constant and consistent damping force along the entire injection process.

There is also a demand for injection devices having a reduced number of components but still having good functionality for self-administration, that are easy to handle and that have penetration and injection force means that can deliver enough power and damping during the whole stroke.

These demands are obtained and solved by the features of the independent patent claims. Preferable embodiments are the subject of the dependent patent claims.

According to a main aspect of the present invention, it is characterized by an injection device comprising a housing, a container arranged inside said housing and containing medicament to be injected through a needle attachable to said container, drive means arranged to be held in a loaded state by a locking means, wherein said drive means are capable of operating on said container for penetrating said needle into an injection site and injecting said medicament when said locking means are released by an activating means, and wherein said injection device comprises a gas spring having a matter-filled housing system, a piston and a piston rod connected to said drive means for driving said drive means with a constant and consistent damping force along its entire stroke length when said locking means are released.

According to another aspect of the present invention, said container is arranged in a container holder which is slidable from a position where the needle is protected inside said housing, to a position where said needle protrudes outside said housing, and wherein said drive means is capable of acting on said holder for performing the penetration of the needle.

According to a further aspect of the present invention, said gas spring is arranged in a tubular member, which is slidable inside said housing, and wherein said tubular member is arranged with a drive plate acting on a plunger rod of said container for performing an injection of said medicament.

According to yet an aspect of the present invention, said tubular member is arranged parallel with, and on the side of, said container.

According to a further aspect of the present invention, said device comprises reloading means connected to the drive means for moving said drive means to its loaded state.

There are several advantages with the present invention. The gas spring provides a smoother, damped and controlled movement of the container and/or plunger rod than an ordinary compression spring, and in particular during the initial movement. Further the force from the gas spring does not decrease with the movement in the same manner as a compression spring does.

The gas spring further provides additional design possibilities such that the gas spring may be placed beside the container, thereby reducing the length of the device. The device becomes somewhat broader, but this is often an advantage for many patients, providing a better grip.

These and other aspects of and advantages with the present invention will become apparent from the following detailed description and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
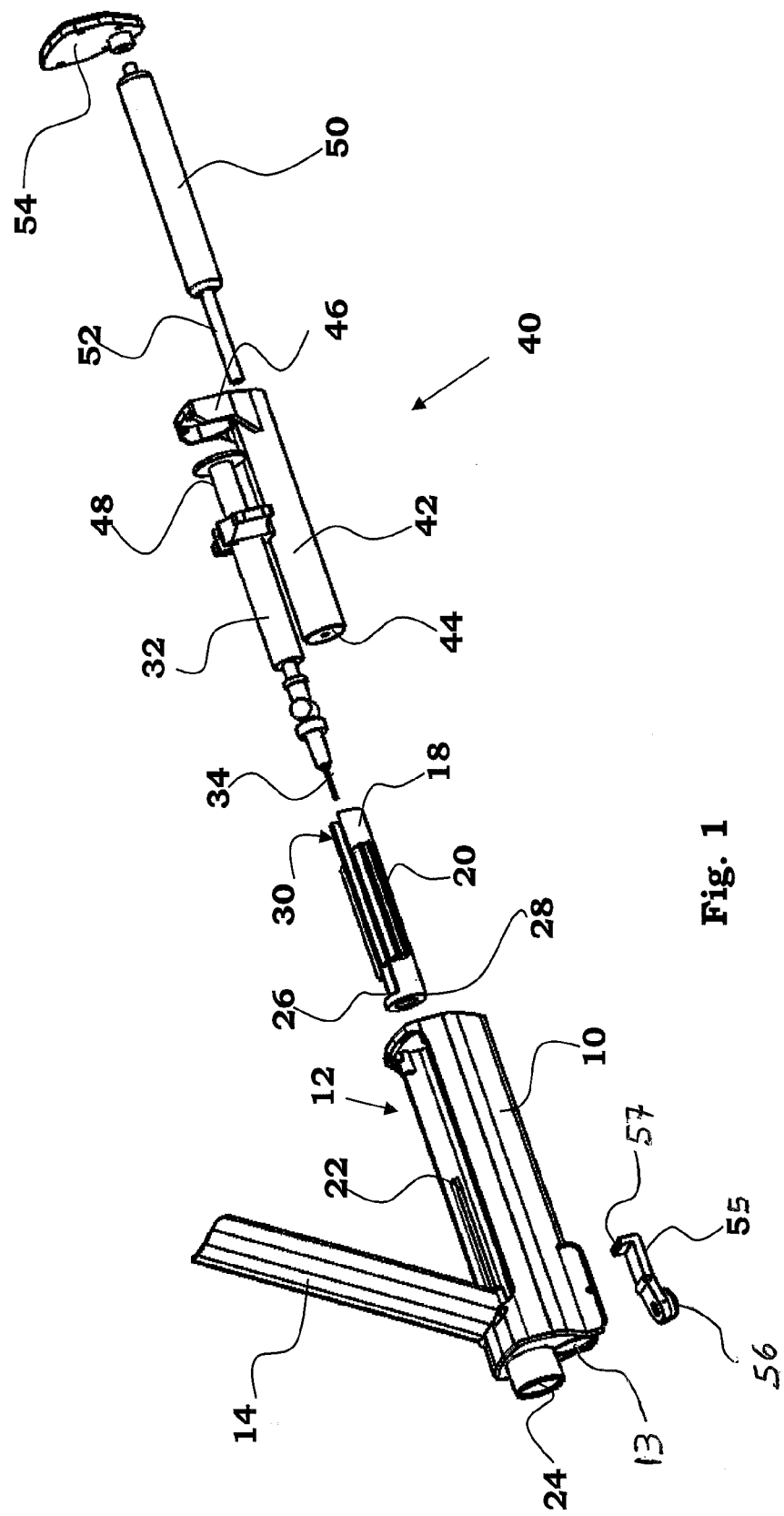
FIG. 1 is an exploded view of a first embodiment of an injection device according to the present invention.

In the drawings, one embodiment of an injection device according to the present invention is shown. It comprises a housing 10 having a somewhat elongated shape, a container 32 arranged inside said housing and containing medicament to be injected through a needle 34 attachable to said container, drive means 40 arranged to be held in a loaded state by a locking means and capable of operating on said container for penetrating said needle into an injection site and injecting said medicament when said locking means are released by an activating means, and a gas spring for driving said drive means. One side of the housing is arranged with an opening 12 having an openable lid 14 attached with hinges 16. Inside the housing a container holder 18 is arranged slidable in the longitudinal direction of the housing with the help of elongated grooves 20 on the container holder mating with elongated ridges 22 on the inner surface of the housing. The drive unit 40 is further arranged in the housing, comprising a generally tubular member 42 placed beside the syringe and parallel with it and slidable with respect to the housing. The front end of the tubular member 42 is arranged with an end wall 44 having a central guide hole. The rear end of the tubular member is open. At the rear end of the tubular member a drive plate 46 is attached and arranged perpendicular to the tubular member and the container. The gas spring 50 having a characteristic that provides a constant and consistent damping force along the entire stroke length, due to its ability to have a controlled rate of extension, i.e. a controlled release of the stored energy, is arranged inside the tubular member 42, wherein the gas spring comprises a matter-filled housing system; e.g. gas-filled, liquid-filled or a combination thereof; a piston with a piston rod 52; a sealing-guiding unit and end fittings. In order to make the gas spring to move a particular load, it must first be compressed, which increases the pressure inside the housing system. The piston rod of an unloaded gas spring is always in an extended position. In order to ensure a damping, e.g. a minor quantity of oil inside the housing may be used to lubricate the seals. The end of the piston rod is fixedly attached in a guide hole of the end wall 44. The rear end of the gas spring, having a guide pin, is in contact with an end cap 54, which in turn is fixedly attached to the housing.

Figure 2:
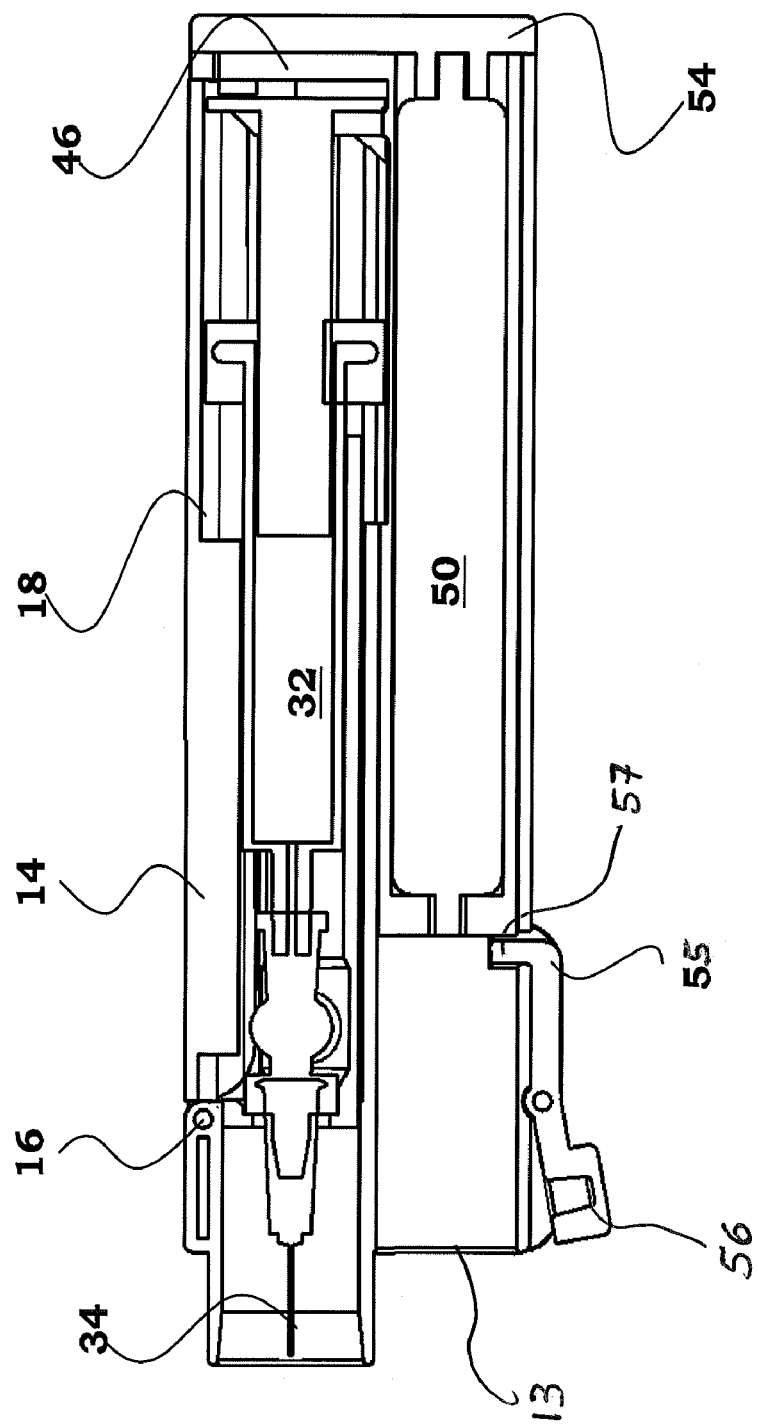
FIG. 2 is a side view in cross-section of the device of FIG. 1 in a state before injection.
Figure 3:
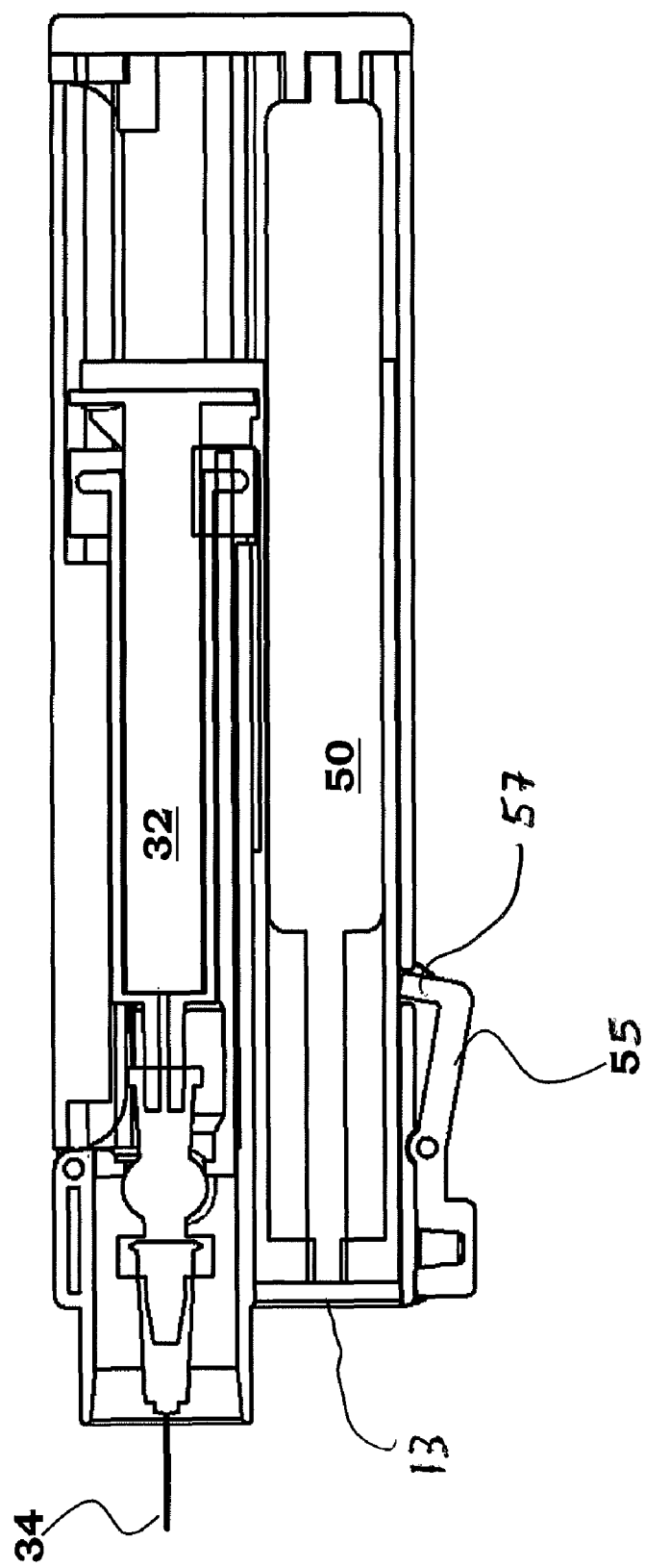
FIG. 3 is a side view in cross-section of the device of FIG. 1 in a state after injection.

In a preferred embodiment, as seen in FIGS. 1-3, the container holder 18 is aligned with a front opening 24 of the housing. The front end of the container holder is arranged with an end surface 26 having central opening 28. The container holder is further open at the opposite end and is arranged with an elongated opening 30 facing the opening of the housing. The container 32; e.g. a cartridge, a syringe or the like; containing medicament to be injected can be placed in the container holder through the opening of the container holder and placed such that a front shoulder of the container is abutting the end surface and with a needle 34 pointing towards the front opening of the housing. The drive plate 46 is designed to be in contact with the rear end of a plunger rod 48 of a syringe. In an alternative embodiment (not shown) a plunger rod is attached at one end to the drive plate, such that the other end of said plunger rod is in contact with a stopper inside a cartridge.

In the preferred embodiment, as seen in FIGS. 1-3, the locking and the activating means 55 in the form of a lever is arranged; e.g. pivotally, slidable; to the housing where one end 57 of the lever is in contact with the end wall 44 of the tubular member 42 acting as the locking means and the other end of the lever is a trigger button 56 acting as the activating means; such that when the end 57 of the lever is in contact with the end wall 44 of the tubular member 42, the drive means 40 and the gas spring are in a loaded state.

Moreover, in the preferred embodiment, the housing 10 comprises reloading means in the form of a through hole 13 extending from the front end and in the longitudinal direction of the housing, wherein the tubular member 42 is arranged to be displaced when the drive means are released from its loaded state, as shown in FIG. 1-3.

Figure 4:
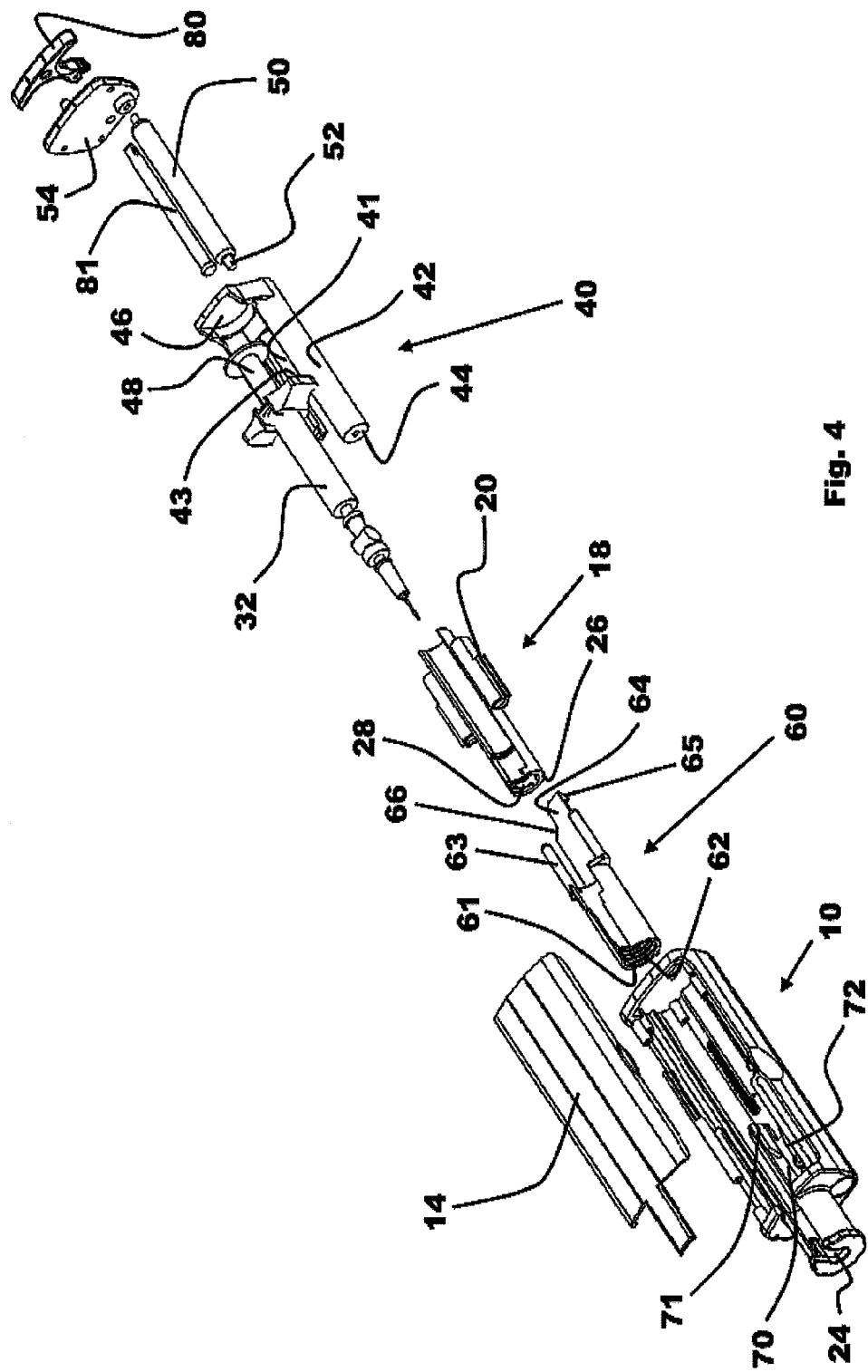
FIG. 4 is an exploded view of a second embodiment of an injection device according to the present invention.

In a second embodiment, as shown in FIG. 4, a needle shield 60 in the form of a tubular sleeve is slidable arranged inside the housing aligned with a front opening 24 of the housing. The front end of the needle shield is slidable arranged with an end surface 61 having central opening 62. The needle shield also comprises two slidable elongated bars 63 slidable arranged in the longitudinal direction of the housing within two elongated grooves 20 on a container holder 18. The needle shield further comprises a first elongated flexible tongue 64 extending rearwards in the longitudinal direction of the housing, wherein the first flexible tongue 64 comprises a heel 66 and a radial outwardly protruding first ledge 65.

In the second embodiment, the drive means 40 further comprises a second elongated flexible tongue 41 extending forwards in the longitudinal direction of the housing, wherein the second flexible tongue 41 comprises radial inwardly protruding second ledge 43. Moreover, the drive unit also comprises a third elongated flexible tongue (not shown) extending forwards in the longitudinal direction of the housing, wherein the third flexible tongue comprises a radial outwardly protruding third ledge (not shown) which is arranged to be in contact with a ratchet (not shown) arranged on an inner wall of the housing 10 for providing an audible and tactile feedback to the user when the device is delivering the medicament.

In the second embodiment, as seen in FIG. 4, the locking and the activating means 70 in the form of a lever is arranged; e.g. pivotally, slidable; to the housing where one end 72 of the lever in contact with the end wall 44 of the tubular member 42 acting as the locking means and the other end 71 of the lever is arranged to be in contact with the first elongated flexible tongue 64 of the needle shield 60 acting as the activating means; such that when the end 72 of the lever is in contact with the end wall 44 of the tubular member 42, the drive means 40 and the gas spring are in a loaded state.

In the second embodiment, as seen in FIG. 4, a reloading means, comprising a pulling handle 80 and a slidable and resilient pulling rod 81 having a rear end and a forward end, is arranged to the drive means 40 for moving said drive means to its loaded state and thereby reloading the gas spring. The pulling rod is adapted to pass through a through hole (not shown) on the surface of the drive plate 46 and through a through hole (not shown) on the surface of the end cap 54. The rear end is connected to the pulling handle and the forward end has a circular ledge which has a larger diameter than the through holes such that when the drive unit has to be pulled back against the force exerted by the piston rod 52, the circular ledge is resting against the forward surface of the drive plate 46.

Figure 5:
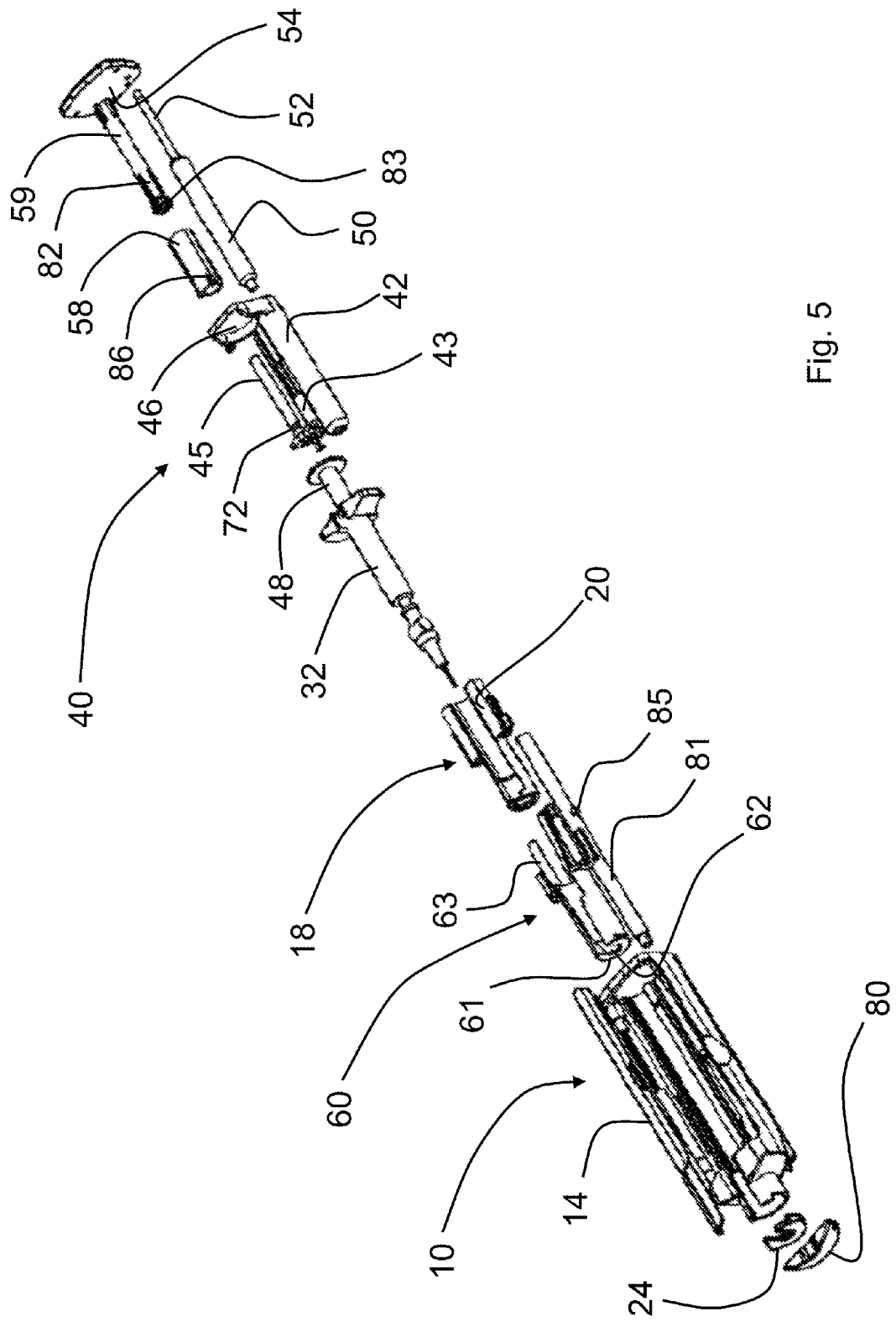

In a third embodiment, as shown in FIG. 5, the end of the piston rod 52 is fixedly attached to the inner surface of the end cap 54; and the rear end of the gas spring, having a guide pin, is fixedly attached in a guide hole of an end wall of the generally tubular member 42. A needle shield 60 in the form of a tubular sleeve is slidable arranged inside the housing aligned with a front opening 24 of the housing. The front end of the needle shield is slidable arranged with an end surface 61 having central opening 62. The needle shield also comprises two slidable elongated bars 63 slidable arranged in the longitudinal direction of the housing within two elongated grooves 20 on the container holder 18. The needle shield further comprises an elongated tongue 64 extending rearwards in the longitudinal direction of the housing.

In the third embodiment, the generally tubular member 42 of the drive means 40 comprises a radial outwardly protruding second ledge 43 and an elongated rod 45 extending forwards in the longitudinal direction of the housing from the protruding second ledge 43. Moreover, the outer wall of the elongated rod 45 is arranged with a ring-shaped recess 72 nearest the protruding second ledge 43.

As seen in FIG. 5, the locking and the activating means in the form of a first slidable tubular sleeve 58 comprising an outwardly protruding ledge 85 is arranged around a second tubular sleeve 59. Said second tubular sleeve 59 is fixedly attached at its rear end to the inner surface of an end cap 54, and is provided with a number of elongated slots at its front end, thereby forming a number of resilient arms 82. The ends of the arms 82 are arranged with outwardly directed projections 83 abutting the inner wall of the first tubular sleeve 58. Further, the ends of the arms 82 are arranged inwardly directed projections (not shown) abutting the outer wall of the elongated rod 45. The second tubular sleeve 59 is arranged to receive the elongated rod 45. A resilient means as e.g. a spring, (not shown) is arranged around the second tubular sleeve 59 and between the inner surface of the end cap 54 and the inner surface of a wall arranged at the front end of the first tubular sleeve 58. When the elongated rod 45 is arranged within the second tubular means 59, the first tubular sleeve is forced towards the front end of the device due to force exerted by the resilient means whereby the first tubular sleeve covers the arms 82 forcing the inwardly directed projections of the second tubular means 59 inwardly within the ring-shaped recess 72 of the elongated rod 45 acting as the locking means, such that the drive means 40 and the gas spring are in a loaded state. The flexible tongue 64 of the needle shield is arranged to make contact with the outwardly protruding ledge 85 when the needle shield is pushed against an injection site, acting as the activating means.

In the third embodiment, as seen in FIG. 5, a reloading means, comprising a pulling-and-pushing handle 80 and a slidable pulling-and-pushing rod 81, is arranged to the drive means 40 for moving said drive means from an unloaded state to a loaded state and thereby reloading the gas spring. The pulling-and-pushing rod is adapted to pass through a through hole (not shown) on the front surface of the housing 10 and through a through hole (not shown) of the drive plate 46. The front end is connected to the pulling-and-pushing handle and a protrusion 85 is arranged on its elongated outer surface at a predetermined distance from its front end such that when the drive unit has to be pushed back against the force exerted by the piston rod 52, the pulling-and-pushing handle is pulled towards the front end of the device, is clockwise rotated and is pushed against a surface as e.g. a table or the like.

The device is intended to function as follows.

When a patient is to inject a dose of medicament, the lid 14 is opened and a container 32 is placed in the container holder. Before insertion, the patient may have performed different actions such as mixing if the medicament has to be mixed before delivery or priming in order to remove any entrapped air and/or needle setting if the container is a cartridge. The lid is then closed and the device is ready for use, FIG. 2.

In the preferred embodiment, the front end of the injector is then pressed against the injection site and the trigger button 56 is then pushed whereby the lever resting against the tubular member 42 is moved out of contact releasing the drive means from its loaded state due to the constant and consistent damping force exerted by the gas spring. The movement of the drive means causes the container 32 to slide forward due to the slidable arrangement of the container holder 18. The constant and consistent damping force from the gas spring is transmitted to the plunger rod 48 and because of the incompressibility of the medicament and the small passage of the needle; the needle penetrates the skin of the patient. The movement of the container is stopped when the container holder reaches the front wall of the housing.

The constant and consistent damping force from the gas spring now forces the plunger rod forward, whereby the medicament is injected into the patient with a uniform force, FIG. 3. When the injection is completed the device is removed from the injection site. The container is removed from the device, and the drive means is pushed back to its original position by a rod-shaped means introduced through the through hole 13 in a suitable manner against the force exerted by the piston rod 52 whereby the drive means 40 are moved backwards and locked when the means 57 are engaged with the wall 44. A new container may now be placed in the device.

In the second embodiment, as shown in FIG. 4, the front end of the needle shield is pressed against the injection site whereby the heel 66 is slid over the end 71 forcing the locking and activating means 70 to be moved, e.g. pivoted, for releasing the contact of the end 72 with the wall 44 of the tubular member 42. The constant and consistent damping force from the gas spring 50 is then free to move the tubular member in the forward direction, whereby also the drive plate 46 is moved. The movement of the drive plate causes the container 32 to slide forward due to the slidable arrangement of the container holder 18. The constant and consistent damping force from the gas spring is transmitted to the plunger rod 48 and because of the incompressibility of the medicament and the small passage of the needle; the needle penetrates the skin of the patient. The movement of the container is stopped when the container holder reaches the front wall of the housing.

Further, the constant and consistent damping force from the gas spring forces the plunger rod forward, whereby the medicament is injected into the patient with a uniform force.

When the injection is completed the device is removed from the injection site and the needle shield is extended over the needle. The container is removed from the device and the tubular member and the needle shield are pulled back to its original position against the force exerted by the piston rod 52 by pulling the handle 80. The drive unit 40 is moved backwards and locked when the means 71 is engaged with the wall 44. A new container may now be placed in the device.

Moreover, when the needle shield is pushed against the injection site and the drive unit 40 is moved forward, the radial inwardly protruding second ledge 43 comes into contact with the radial outwardly protruding first ledge 65 for allowing the needle shield to be pulled back.

In the third embodiment, as shown in FIG. 5, the front end of the needle shield is pressed against the injection site whereby the flexible tongue 64 of the needle shield makes contact with the outwardly protruding ledge 85 and thereby pushing rearward the first slidable tubular sleeve 58. When the first slidable tubular sleeve 58 moves rearwards, the resilient arms 82 moves radially outwards releasing the inwardly directed projections from the ring-shaped recess 72 of the elongated rod 45, whereby the constant and consistent damping force from the gas spring 50 is then free to move the tubular member 42 in the forward direction, whereby also the drive plate 46 is moved. The movement of the drive plate causes the container 32 to slide forward due to the slidable arrangement of the container holder 18. The constant and consistent damping force from the gas spring is transmitted to the plunger rod 48 and because of the incompressibility of the medicament and the small passage of the needle; the needle penetrates the skin of the patient. Further, the constant and consistent damping force from the gas spring forces the plunger rod forward, whereby the medicament is injected into the patient with a uniform force. The movement of the container is stopped when the container holder reaches the front wall of the housing.

When the injection is completed the device is removed from the injection site and the needle shield is extended over the needle. The container is removed from the device and the tubular member 42 and the needle shield are pushed back to its original position against the force exerted by the piston rod 52 by the pulling-and-pushing handle 80. For locking the drive unit, the drive unit 40 is moved backwards until the inwardly directed projections of the resilient arms 82 engages the ring-shaped recess 72 of the elongated rod 45, forcing the resilient arms 82 to move radial inwardly and allowing the first tubular sleeve to slide towards the front end of the device due to the force exerted by the resilient means. A new container may now be placed in the device.

It is to be understood that the device may be modified in many ways and arranged with additional features. Thus, the trigger may have many different designs, including extra safety members requiring a two-step or two-grip action in order to activate the device.

It is thus to be understood that the embodiments described above and shown in the drawings is to be regarded as only non-limiting examples of the present invention and that it may be modified in many ways within the scope of protection of the patent claims.

The invention claimed is:

1. An injection device, comprising:
a housing;
a container arranged inside said housing and containing medicament to be injected through a needle attachable to said container;
a drive mechanism, comprising a drive plate and a tubular member arranged parallel with, and on a side of, the container;
a locking mechanism arranged to hold the drive mechanism in a loaded state;
an activating mechanism configured to release the locking mechanism;
wherein the drive mechanism is arranged to operate on the container for penetrating the needle into an injection site and injecting the medicament when the locking mechanism is released by the activating mechanism;
a gas spring arranged inside the tubular member and comprising a rear end fixedly attached to an end cap which is fixedly attached to the housing and a forward end of a piston rod fixedly attached to an end wall of the tubular member, wherein the gas spring has a constant and consistent damping force characteristic for driving the drive mechanism with a constant and consistent damping force along its entire stroke length when the locking mechanism is released; and
a reloading mechanism connected to the drive mechanism and configured to move the drive mechanism to the loaded state and thereby reload the gas spring;
wherein the container is arranged in a container holder, the container holder from a first position, in which the needle is protected inside the housing, to a second position, in which the needle protrudes outside the housing, and the drive mechanism is configured to act on the container holder for performing the penetration of the needle.

2. The injection device of claim 1, wherein the drive plate is arranged to act on a plunger rod of the container for performing the injection of the medicament.

3. The injection device of claim 1, wherein the drive plate has a plunger rod which acts on a stopper within the container for performing an injection of the medicament.

4. The injection device of claim 1, wherein the drive plate is arranged to act on a plunger rod of the container for performing the injection of the medicament.

5. The injection device of claim 1, wherein the drive plate has a plunger rod which acts on a stopper within the container for performing the injection of the medicament.

* * * * *